United States Patent [19]

Epstein et al.

[11] Patent Number: 4,916,137

[45] Date of Patent: Apr. 10, 1990

[54] 5-(SUBSTITUTED-AMINO)-8-(PHENYL OR SUBSTITUTED-PHENYL)-3H,6H-1,4,5A,8A-TETRAAZAACENAPHTHYLEN-3-ONES AND TREATMENT OF NEURAL BEHAVIOR DISORDERS

[75] Inventors: Joseph W. Epstein, Monroe; Jeremy I. Levin, Spring Valley, both of N.Y.; Shin S. Tseng, Bridgewater, N.J.

[73] Assignee: American Cyanamid Company, Wayne, N.J.

[21] Appl. No.: 278,296

[22] Filed: Nov. 30, 1988

Related U.S. Application Data

[63] Continuation-in-part of Ser. No. 158,448, Feb. 22, 1988, abandoned.

[51] Int. Cl.[4] ................ H61K 31/505; C07D 239/00; C07D 413/00
[52] U.S. Cl. .................................... 514/267; 544/251; 544/115; 540/600; 514/212; 514/233.2
[58] Field of Search ................ 544/251, 115; 514/212, 514/233.2, 267; 540/600

[56] References Cited

U.S. PATENT DOCUMENTS 4,713,383 12/1987 Francis et al. ...................... 544/251

FOREIGN PATENT DOCUMENTS 674585 11/1963 Canada ................................ 544/251

*Primary Examiner*—Mary C. Lee
*Assistant Examiner*—Robert C. Whittenbaugh
*Attorney, Agent, or Firm*—Kenneth J. Dow

[57] ABSTRACT

This disclosure described novel 5-(substituted-amino)-8-(substituted-phenyl)-3H,6H, -1,-4,5a,8a-tetraazaacenaphthylen-3-ones useful for the treatment of cognitive and related neural behavioral disorders in mammals.

18 Claims, No Drawings

5-(SUBSTITUTED-AMINO)-8-(PHENYL OR SUBSTITUTED-PHENYL)-3H,6H-1,4,5A,8A-TETRAAZAACENAPHTHYLEN-3-ONES AND TREATMENT OF NEURAL BEHAVIOR DISORDERS

CROSS REFERENCE TO RELATED APPLICATION

This application is a continuation-in-part of our copending application Ser. No. 07/158,448, filed Feb. 22, 1988, now abandoned.

BRIEF SUMMARY OF THE INVENTION

The present invention relates to new organic compounds and, more particularly, is concerned with novel 5-(substituted-amino)-8-(phenyl or substituted-phenyl)-3H,6H-1,4,5a,8a-tetraazaacenaphthylen-3-ones which are useful as agents for the treatment of cognitive and related neural behavioral disorders in mammals.

The novel compounds of the present invention may be represented by the following structural formula:

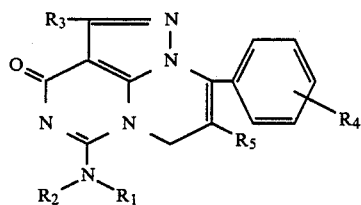

wherein $R_1$ and $R_2$ are each individually selected from the group consisting of hydrogen, alkyl($C_1$–$C_4$), benzoyl, mono or disubstituted benzoyl wherein the substituents are alkyl($C_1$–$C_6$), alkoxy($C_1$–$C_6$), acyloxy($C_2$–$C_7$), halogen, nitro or trifluoromethyl, and moieties of the formulae:

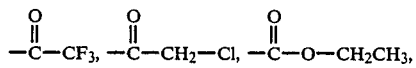

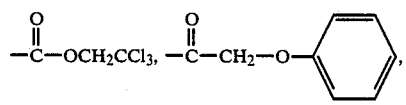

or —$(CH_2)_n$—R wherein n is an integer from 1 to 3 and R is hydroxy, 4-morpholinyl, 1H-imidazol-1-yl, —CH[alkoxy($C_1$–$C_3$)]$_2$, α-hydroxybenzyl, phenyl or mono or disubstituted phenyl wherein the substituents are halogen or alkyl ($C_1$–$C_6$); $R_1$ and $R_2$ taken together with their associated N(itrogen) is 4-morpholinyl or a moiety of the formula: —N(CH$_2$)$_m$ wherein m is an integer from 2 to 6; $R_3$ is hydrogen or alkyl($C_1$–$C_6$); $R_4$ is hydrogen, halogen, alkyl($C_1$–$C_3$), alkoxy($C_1$–$C_3$) or trifluoromethyl; and $R_5$ is hydrogen or alkyl($C_1$–$C_6$). For purposes of this invention, halogen may be fluorine, chlorine, bromine or iodine.

This invention also pertains to new compositions of matter containing the above-defined, novel 5-(substituted-amino)-8-(phenyl or substituted-phenyl)-3H,6H-1,4,5a,8a-tetraazaacenaphthylen-3-one compounds which are useful as agents for the treatment of cognitive and related neural behavioral disorders in mammals and to the chemical synthesis of the novel compounds disclosed herein.

DETAILED DESCRIPTION OF THE INVENTION

The novel compounds of the present invention are obtainable as white to brown crystalline materials having characteristic melting points and absorption spectra. In general, they are soluble in organic solvents such as trifluoracetic acid or dimethyl sulfoxide and the like and are sparingly soluble in solvents such as N,N-dimethylformamide or chloroform and the like but are generally insoluble in water.

The novel 5-(substituted-amino)-8-(phenyl or substituted-phenyl)-3H,6H-1,4,5a,8a-tetraazaacenaphthylen-3-one compounds of the present invention may be readily prepared as set forth in the following reaction schemes.

Scheme 1

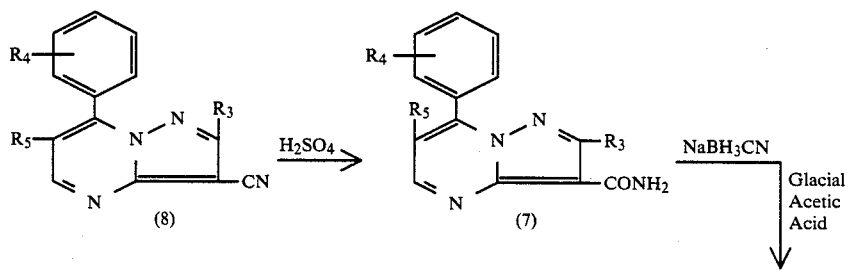

Scheme 1

-continued

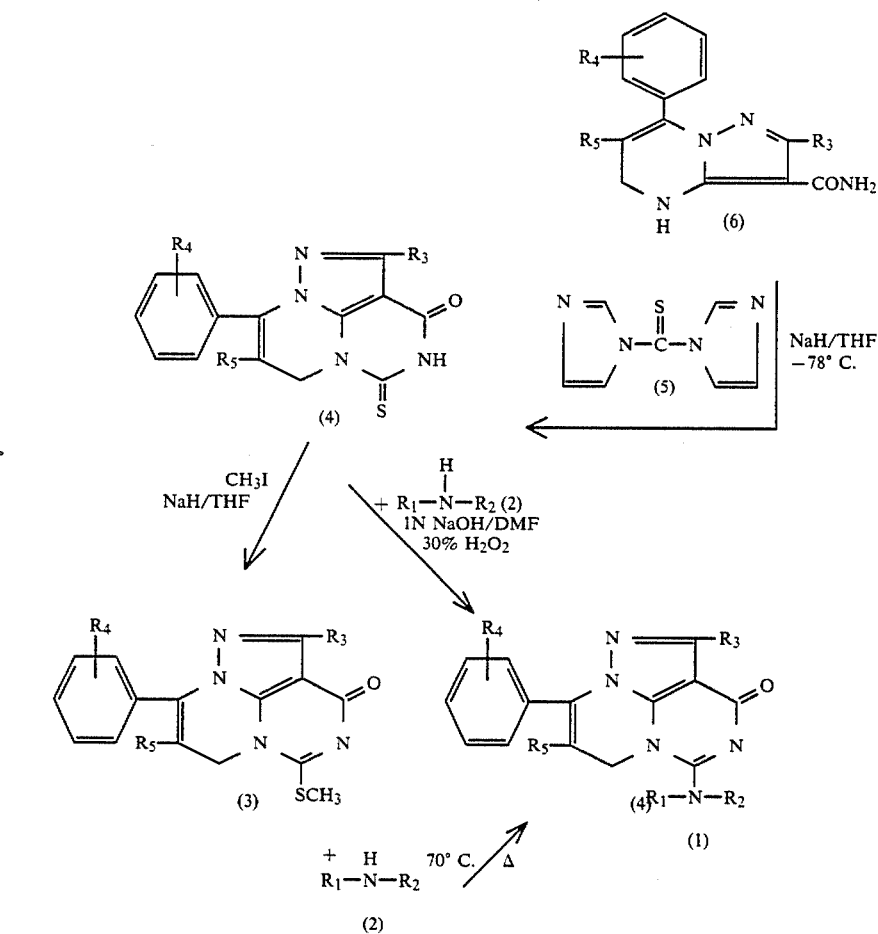

wherein $R_1$, $R_2$, $R_3$, $R_4$ and $R_5$ are as hereinabove defined.

In accordance with the above reaction scheme (Scheme 1), an appropriately 7-substituted pyrazolo[1,5-a]-pyrimidine-3-carbonitrile (8) prepared as described herein and in U.S. Pat. No. 4,236,005 is converted to the corresponding 7-substituted pyrazolo[1,5-a]pyrimidine-3-carboxamide (7) by reaction with a strong mineral acid, such as sulfuric acid followed by reaction with water; then any excess acid is neutralized. The 3-carboxamide compound (7) is then reacted with sodium cyanoborohydride by stirring in glacial acetic acid under nitrogen in an ice bath for approximately one hour, then at room temperature for from 1-12 hours. The resulting precipitate is collected, washed with water, dissolved in an inert solvent such as dichloromethane or acetonitrile and the like and washed with a saturated solution of sodium bicarbonate. Separation and evaporation of the organic phase gives the 4,5-dihydro-7-substituted pyrazolo[1,5-a]pyrimidine-3-carboxamide intermediate compound (6) which is recrystallized from solvents such as isopropyl alcohol or acetonitrile and the like or from a mixture of solvents such as etherhexane, chloroform-methanol or N,N-dimethylformamide-acetonitrile and the like. The reduced 7-substituted pyrazolo[1,5-a]pyrimidine-3-carboxamide (6) in an inert solvent such as dry tetrahydrofuran or p-dioxane and the like is stirred with a strong base such as sodium hydride, lithium diisopropylamide, or potassium amide under nitrogen or argon at a temperature of about −78° C. bath) for 20 minutes to 3 hours, then 1,1′-thiocarbonyldiimidazole (5) or thiophosgene is added and the reaction mixture is stirred in the cold for one to 3 hours, then is allowed to reach room temperature with stirring for 24–48 hours. The reaction mixture is quenched with water and neutralized to pH 7.0 with 5% aqueous hydrochloric acid. The 4,5-dihydro-5-thioxo-8-(substituted), 3H,6H-1,4,5a,8a-tetraazaacenaphthylen-3-one compound (4) is recovered by precipitation, or by extraction with a solvent such as chloroform or ether and the like, followed by evaporation of the solvent. To a solution of the 5-thioxo compound (4) in a solvent such as N,N-dimethylformamide and the like is added 1 equivalent of 1N sodium hydroxide, the reaction mixture is cooled to 0° C. in an ice bath and 3 equivalents of 30% hydrogen peroxide are added dropwise. The reaction mixture is stirred at 0° C. for about 30 minutes, then the appropriate primary aliphatic amine selected from those such as ethanolamine, methylamine, ethylamine, isopropylamine, n-butylamine, isobutylamine, aminoacetaldehyde dimethyl acetal, isopropylamine, 2-methylbenzylamine, 4-chlorobenzylamine, benzylamine, sec-butylamine, 2-amino- 1-phenyl ethanol, N-(2-aminoethyl) morpholine, 1-imidazolylpropylamine and the like or a cyclic secondary amine such as pyrrolidine or piperidine and the like is added in one portion and the stirred reaction mixture is allowed to warm to room temperature for several hours, then is filtered to collect the precipitated 5-[(substituted)amino]-8-phenyl or [(substituted)phenyl]-3H,6H-1,4,5a,8a-tetraazaacenaphthylen-3-one product (1) which is washed with water then with ether.

Alternatively, the 5-thioxo compound (4) is dissolved in a solvent such as dry tetrahydrofuran and the like, then is stirred with sodium hydride at 0° C. for about 15 minutes and this mixture is treated with an excess of methyl iodide and allowed to warm to room temperature with stirring for 3 hours. Then the mixture is quenched with water and extracted into a solvent such as chloroform and the like. Evaporation of the solvent gives the 5-methylthio-8(substituted)-3H,6H-1,4,5a,8a-tetraazaacenaphthylen-3-one compound (3). The 5-methylthio compound (3) is suspended in a primary aliphatic amine such as benzylamine or 4-chlorobenzylamine and the like, then the mixture is heated at 70° C. for from 12 to 48 hours. The reaction mixture is cooled, then filtered to collect the solid which is washed with ether to give the 5[(substituted)-amino]-8-phenyl or [(substituted)phenyl]-3H,6H-1,4,5a,8a-tetraazaacenaphthylen-3-one product (1).

the addition of cyanogen bromide, and reaction at −78° C. for about 4 hours and then at room temperature for 16 hours. The reaction mixture is diluted with water and the product (1) where R1 and R2 are both hydrogen is collected by filtration, then washed with water and ether. When a suspension of the product (1) in dry tetrahydrofuran is heated at reflux for 16 hours in the presence of [1,8-bis(dimethylamino) naphthalene, N,N,N',N'-tetramethyl-1,8-naphthalenediamine] and an acid chloride such as 2,2,2-trichloroethyl chloroformate or chloroacetyl chloride and the reaction mixture is quenched with water the products (1a) are obtained.

When the above product (1) is suspended in an acid anhydride such as trifluoroacetic anhydride and heated at reflux for about 24 hours, then the reaction mixture is filtered and the precipitate is washed with ether and chloroform and the organic solution is separated, washed with saturated sodium bicarbonate, dried and concentrated, the product 1b is obtained.

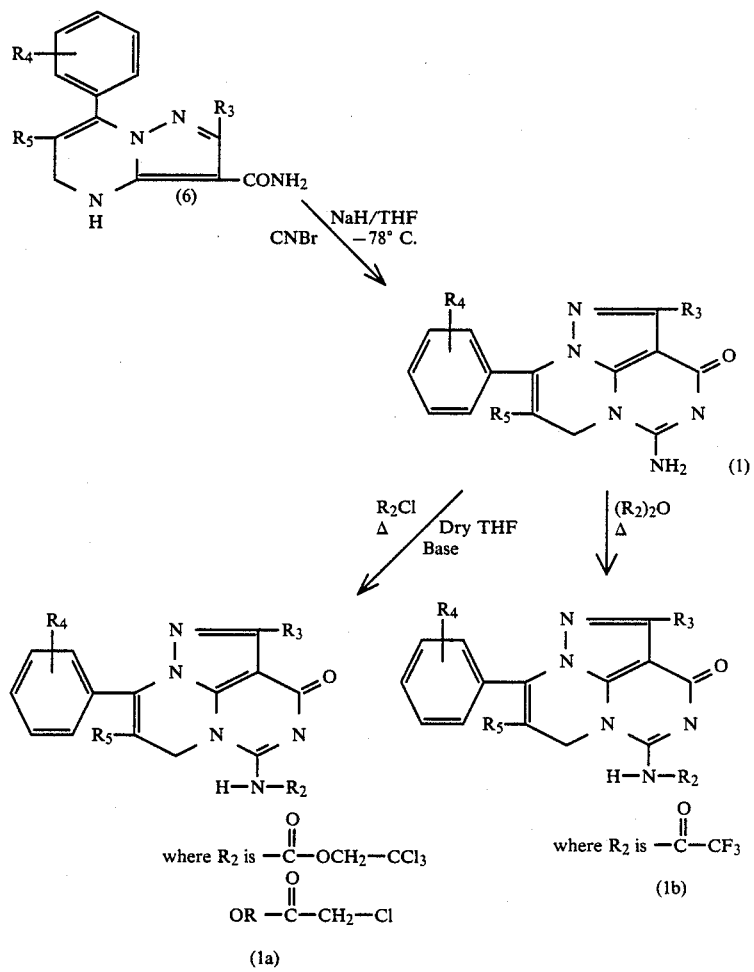

In accordance with Scheme 2, where R3, R4 and R5 are as hereinbefore defined, the reduced 7-substituted pyrazolo[1,5-a]pyriimidine-3-carboxamide (6) prepared as described in Scheme 1 is dissolved in dry tetrahydrofuran and cooled to −78° C. The mixture is then treated with sodium hydride for about 30 minutes, followed by

Scheme 3

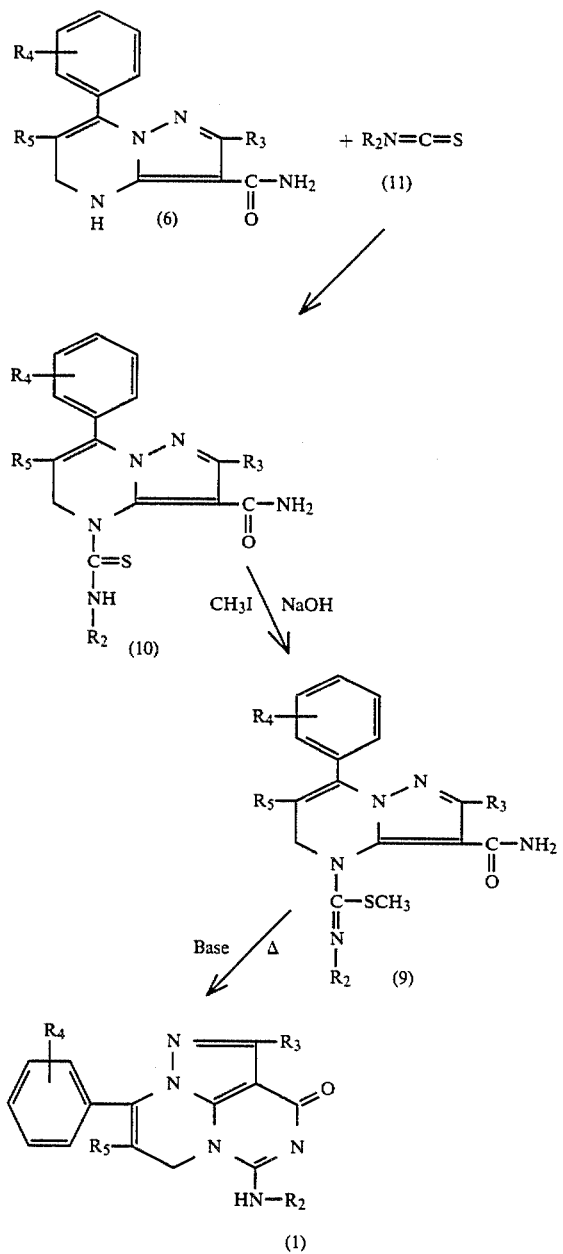

In accordance with Scheme 3, where $R_3$, $R_4$ and $R_5$ are as hereinbefore defined, an appropriately substituted reduced 7-substituted pyrazolo [1,5-a] pyriimidine-3-carboxamide (6) prepared as described in Scheme 1 is reacted with an excess of an appropriate $R_2$ isothiocyanate (11) such as benzoyl isothiocyanate in dry acetone under nitrogen. The mixture is heated at reflux for about 20 hours then cooled and filtered to obtain the 4-[(benzolyamino)thioxomethyl]-pyrazolo[1,5-a]pyrimidine carboxamide (10). The compound (10) in N,N-dimethylformamide is combined with 1N sodium hydroxide and is then treated with methyl iodide to obtain the corresponding -4(5H)-carboimidothioic acid, methyl ester (9) from an aqueous mixture. The methyl ester (9) in p-dioxane in the presence of 7N sodium hydroxide is refluxed for several hours and then is neutralized with 6N hydrochloric acid to precipitate the desired [3oxo-3H,6H-1,4,5a,8a-tetraazaacenaphthylen-5-yl]benzamide product (1).

Alternatively, an appropriate carboxamide (6) in dry tetrahydrofuran is cooled to −78° HC and is stirred with sodium hydride for about one hour and then an appropriate isothiocyanate (11) such as ethoxycarbonyl isothiocyanate is added and the reaction mixture is stirred at −78° C. for several hours longer. Then, stirring is continued at room temperature for 48 hours. The reaction is quenched with water, extracted with ether, and the aqueous layer is neutralized with 5% hydrochloric acid and extracted with a solvent such as chloroform to obtain the desired product (1).

The novel compounds of the present invention possess the ability to enhance neural function in warm-blooded animals affected by behavioral neurological problems, including the cognitive deterioration associated with decreased neural function which occurs with cerebral insufficiency, aging, dementia, and similar conditions.

A useful in vivo test that measures how effectively central nervous system-acting drugs enhance survival in a hypoxic environment, presumably by improving the ratio of energy supply to demand is known as the Hypoxic Survival Test. This test demonstrates the activity of the test compound relative to a known reference compound such as physostigmine. This test shows the enhanced survival of test animals in a hypoxic environment after treatment with drug as compared to saline treated control animals without drug. Extensive testing has demonstrated that under conditions of 10% oxygen, only 5–20% of control mice (treated with saline) survive after 5 minutes, whereas 60–80% of the reference compound treated mice survive. Drugs are tested by intraperitoneally injecting groups of mice 30 minutes prior to placing them in a hypoxic mixture and measuring survival. The rationale of this test is that drugs which enhance survival under hypoxic conditions without concomitment, depression or sedative side effects, may do so by enhancing energy metabolism, or by preserving normal brain function under conditions of reduced energy metabolism. Given the dependence of the brain on a constant supply of energy, drugs which have this property may have many far-reaching therapeutic indications, including recovery from stroke and closed head injury, as well as reducing the deleterious effects of the aging central nervous system. For example, in aged and senile demented patients, energy metabolism is known to be deficient, and is thought to contribute significantly to the neurochemical and neurophysiological dysfunctions of aging.

Groups of 20 Royal Hart mice (6–8 weeks of age) are given intraperitoneal injections with test compound normally at 10 and 100 mg/kg 30 minutes prior to placing them in a hypoxic mixture (10% oxygen, 90% carbon dioxide) and measuring survival after 5 minutes. At times further testing may require doses ranging from 1–200 mg/kg.

A separate group of 20 mice is given intraperitoneal injections with saline solution (0.01 cc/g of body weight) and processed as described above.

Still another group of 20 mice is given intraperitoneal injections with a known active dose of the reference compound, e.g., 0.125 mg/kg of physostigmine and processed as described above.

Results of this test on representative compounds of the present invention are reported in Table I.

TABLE I

Hypoxic Survival Test

| Compound | Dose mg/kg | % Survivors |
|---|---|---|
| [3-Oxo-8-[3-(trifluoromethyl)phenyl]3H,6H-1,4,5a,8a-tetraazaacenaphthylen-5-yl]carbamic acid ethyl ester | 100 | 40 |
| 5-(2-Methylpropyl)-8-[3-(trifluoromethyl)phenyl]-3H,6H-1,4,5a,8a-tetraazaacenaphthylen-3-one | 50 | 50 |
| 5-Amino-8-[3-(trifluoromethyl)phenyl]-3H,6H-1,4,5a,8a-tetraazaacenaphthylen-3-one | 50 | 60 |
|  | 100 | 67.5 |
|  | 200 | 60 |
| N-[3-Oxo-8-[3-(trifluoromethyl)phenyl]3H,6H-1,4,5a,8a-tetraazaacenaphthylen-5-yl]-3-(trifluoromethyl)benzamide | 10 | 45 |
|  | 100 | 70 |
| 3-Nitro-N-[3-oxo-8-[3-(trifluoromethyl)phenyl]-3H,6H-1,4,5a,8a-tetraazaacenaphthylen-5-yl]benzamide | 100 | 70 |
| 3,4-Dichloro-N-[3-oxo-8-[3-(trifluoromethyl)phenyl]-3H,6H-1,4,5a,8a-tetraazaacenaphthylen-5-yl]benzamide | 100 | 60 |
| 5-Ethylamino-8-[3-(trifluoromethyl)phenyl]-3H,6H-1,4,5a,8a-tetraazaacenaphthylen-3-one | 100 | 65 |
| 2,2,2-Trifluoro-N-[3-oxo-8-[3-(trifluoromethyl)phenyl]-3H,6H-1,4,5a,8a-tetraazaacenaphthylen-5-yl]acetamide | 100 | 42.5 |
| [3-Oxo-8-[3-(trifluoromethyl)phenyl]3H,6H-1,4,5a,8a-tetraazaacenaphthylen-5-yl]-2,2,2-trichloroethyl ester carbamic acid | 100 | 55 |
| 5-[(2,2-Dimethoxyethyl)amino]-8-[3-(trifluoromethyl)phenyl]-3H,6H-1,4,5a,8a-tetraazaacenaphthylen-3-one | 100 | 60 |
| 5-[[2-(4-Morpholinyl)ethyl]amino]-8-[3-(trifluoromethyl)phenyl]-3H,6H-1,4,5a,8a-tetraazaacenaphthylen-3-one | 100 | 45 |
| 5-[(2-Hydroxy-2-phenylethyl)amino]-8-[3-(trifluoromethyl)phenyl]-3H,6H-1,4,5a,8a-tetraazaacenaphthylen-3-one | 10 | 42.5 |
|  | 100 | 70 |
| 5-[(2,2-Dimethoxyethyl)amino]-8-phenyl-3H,6H-1,4,5a,8a-tetraazaacenaphthylen-3-one | 25 | 55 |
|  | 50 | 40 |
|  | 100 | 55 |
| 5-(Butylamino)-8-phenyl-3H,6H-1,4,5a,8a-tetraazaacenaphthylen-3-one | 50 | 40 |
|  | 100 | 70 |
|  | 200 | 60 |
| 5-(Ethylamino)-8-phenyl-3H,6H-1,4,5a,8a-tetraazaacenaphthylen-3-one | 100 | 72.5 |
|  | 200 | 65 |
| 5-[[(4-Chlorophenyl)methyl]amino]-8[3-(trifluoromethyl)phenyl]-3H,6H-1,4,5a,8a-tetraazaacenaphthylen-3-one | 100 | 55 |
| 5-[(2-Hydroxyethyl)amino]-8-phenyl-3H,6H-1,4,5a,8a-tetraazaacenaphthylen-3-one | 100 | 60 |
| 5-(Methylamino)-8-phenyl-3H,6H-1,4-5a,8a-tetraazaacenaphthylen-3-one | 100 | 95 |
| 5-(Butylamino)-8-[3-(trifluoromethyl)phenyl]-3H,6H-1,4,5a,8a-tetraazaacenaphthylen-3-one | 100 | 57.5 |
| 5-[[(2-Hydroxyethyl)amino]-8-[3-(trifluoromethyl)phenyl]-3H,6H-1,4,5a,8a-tetraazaacenaphthylen-3-one | 100 | 80 |
| 5-[[(2-Methylphenyl)methyl]amino]-8-[3-(trifluoromethyl)phenyl]-3H,6H-1,4,5a,8a-tetraazaacenaphthylen-3-one | 25 | 47.5 |
|  | 50 | 52.5 |
|  | 100 | 70 |
| 5-(Ethylamino)-8-(3-fluorophenyl)-3H,6H-1,4,5a,8a-tetraazaacenaphthylen3-one | 10 | 55 |
|  | 100 | 55 |

Another in vivo test associated with decreased neural function in mammals is the Passive-Avoidance Anoxic-Induced-Amnesia Test. This test is used to determine the attenuation of anoxic induced amnesia in mice treated with drug, as compared to saline treated control animals with no drug.

A shock-motivated, single trial, step-through passive avoidance procedure is used. Groups of 25 Royal Hart and Taconic Farms, middled-aged mice (9 months of age) are placed singly in the front chamber of a 2-chamber box and are allowed to voluntarily cross into the rear chamber. As soon as the mouse enters the rear chamber, a door automatically traps the animal and a mild electric shock (0.4 mA for 4 seconds) is delivered to its feet. Following the foot shock, the mice are initially placed in an anoxic environment (0% oxygen) for 12 seconds, which quickly induces unconsciousness. They are then placed in a hypoxic environment (15% oxygen) for four minutes which allows the mice to resuscitate slowly. All testing is performed 24 hours later, and in all cases the mice appear fully recovered from the previous anoxic/hypoxic treatment. All test compounds are administered intraperitoneally at doses ranging from 10–200 mg/kg, (depending on active doses in previous tests), 30 minutes prior to training and testing. Control animals are injected intraperitoneally only with saline at 0.01 cc/g of body weight.

The latency to enter the rear chamber is recorded for both training and testing. Presumably, the more the animal remembers being shocked, the greater it will inhibit going into the rear chamber and the higher will be its latency to re-enter. An improvement of 30% over saline control scores is considered active. The result of this test on representative compounds of the present invention appears in Table II.

TABLE II

Passive Avoidance Anoxic Induced Amnesia Test

| Compound | Dose mg/kg | % Improvement |
|---|---|---|
| 5-(2-Methylpropyl)-8-[3-(trifluoromethyl)phenyl]-3H,6H-1,4,5a,8a-tetraazaacenaphthylen-3-one | 50 | 43.5 |
|  | 100 | 158.0 |
| 5-Amino-8-[3-(trifluoromethyl)phenyl]-3H,6H-1,4,5a,8a-tetraazaacenaphthylen-3-one | 5 | 45.8 |
|  | 10 | 51.8 |
|  | 100 | 53.5 |
| 5-(Butylamino)-8-phenyl-3H,6H-1,4,5a,8a-tetraazaacenaphthylen-3-one | 25 | 64.3 |

The compounds of the present invention has been found to be useful as agents for the treatment of cognitive and related neural behavioral problems in mammals when administered in amounts ranging from about 5 mg to about 200 mg/kg of body weight per day. A preferred dosage regimen for optimum results would be from about 10 mg to about 50 mg/kg of body weight per day and such dosage units are employed that a total of from about 700 mg to about 3.5 g of the active compound for a subject of about 70 kg of body weight are administered in a 24 hour period.

The hereinabove described dosage regimen for treating neural behavioral problems in mammals may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active acompounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be prepared against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following specific examples.

EXAMPLE 1

7-[3-(Trifluoromethyl)phenyl]pyrazolo[1,5-a]-pyrimidine-3-carboxamide

A mixture of 3.0 g of 7-($\alpha,\alpha,\alpha$-trifluoro-m-tolyl)-pyrazolo[1,5-a]pyrimidine-3-carbonitrile (prepared as described in U.S. Pat. No. 4,236,005) and 150 ml of concentrated sulfuric acid was stirred at room temperature for 4 hours. The solution was then carefully poured into ice water with stirring. The white precipitate formed was collected, washed with water and then with saturated sodium bicarbonate until it was neutral. The solid was heated with one liter of isopropyl alcohol and filtered. The white solid was dried in vacuo and gave the product of the example as a colorless solid, m.p. 256°-258° C.

EXAMPLE 2

7-Phenylpyrazolo[1,5-a]pyrimidine-3-carboxamide

A mixture of 4.0 g of 7-phenylpyrazolo[1,5-a]pyrimidine-3-carbonitrile (prepared as described in Example 7 of U.S. Pat. No. 4,236,005) and 40 ml of concentrated sulfuric acid was stirred at room temperature for 16 hours. The solution was then carefully poured into ice with stirring and the mixture was carefully made just basic with concentrated ammonium hydroxide. The solid was collected by filtration and recrystallized from dichloromethane to give pale yellow needles m.p. 236°-238.5° C.

EXAMPLE 3

4,5-Dihydro-7-phenylpyrazolo[1,5-a]pyrimidine-3-carboxamide

A 6.0 g amount of 7-phenylpyrazolo[1,5-a]-pyrimidine-3-carboxamide (prepared as described in Example 2) was stirred under nitrogen as a suspension in 120 ml of glacial acetic acid (cooled in an ice bath) and then 3.5 g of sodium cyanoborohydride was added to the reaction mixture in portions. After one hour of stirring in the ice bath, the mixture was stirred at room temperature for 3.5 hours at which time the original solid dissolved. Stirring was continued for one hour longer then the solution was concentrated in vacuo. Water was added to the residue and a precipitate formed. The precipitate was collected by filtration and then was dissolved in dichloromethane. The organic solution was washed with a saturated solution of sodium bicarbonate, dried over anhydrous sodium sulfate and filtered. The filtrate was evaporated in vacuo to give a solid. The solid was recrystallized from isopropyl alcohol to give 5.0 g of the desired product as a white solid, m.p. 149°-152° C.

EXAMPLE 4

4,5-Dihydro-7-[3-(trifluoromethyl)phenyl]pyrazolo [1,5-a]pyrimidine-3-carboxamide A 10.0 g amount of 7-[3-(trifluoromethyl)-phenyl]-pyrazolo[1,5-a]pyrimidine-3-carboxamide (prepared as described in Example 1) was stirred under nitrogen as a suspension in 120 ml of glacial acetic acid (cooled in an ice bath) and then 5.5 g of sodium cyanoborohydride was added to the reaction mixture in portions with an additional 80 ml of glacial acetic acid. After one hour of stirring in the ice bath, the mixture was stirred at room temperature for 19 hours. The solution was evaporated to dryness, then water was added and the white precipitate which formed was collected by filtration and washed with an aqueous saturated solution of sodium bicarbonate, then with water. The solid was treated with 100 ml of acetonitrile, then was collected by filtration and dried to give 5.25 g of the desired product which was recrystallized from acetonitrile, m.p. 157°-160° C.

EXAMPLE 5

7-(3-Fluorophenyl)pyrazolo[1,5-a]pyrimidine-3-carboxamide

A 131.5 g amount of 7-(m-fluorophenyl) pyrazolo[1,5-a]pyrimidine-3-carbonitrile (prepared as described in U.S. Pat. No. 4,236,005) was dissolved in 500 ml of concentrated sulfuric acid by stirring at room temperature for 18 hours. The solution was then carefully poured into ice water. The precipitate which formed was collected by filtration then washed with 1N sodium hydroxide until pH 7 was achieved, followed by washing with water to remove the excess base. The crystalline material was dried in vacuo to give 136.3 g of the desired product as yellow crystals, m.p. 247°–249° C.

EXAMPLE 6

7-(3-Fluorophenyl)-4,5-dihydropyrazolo[1,5-a]pyrimidine-3-carboxamide

A 136.3 g amount of 7-(3-fluorophenyl) pyrazolo[1,5-a]pyrimidine-3-carboxamide (prepared as described in Example 5) in one liter of glacial acetic acid was stirred at room temperature, then 83.6 g of sodium cyanoborohydride was added portionwise under nitrogen. The mixture was stirred for 16 hours then the precipitated crystals were collected by filtration and triturated with saturated sodium bicarbonate until pH 7–8 was achieved. The crystals were washed with water and dried in vacuo to give 63.0 g of the product as cream-colored crystals, m.p. 122°–125° C.

EXAMPLE 7

4,5-Dihydro-8-phenyl-5-thioxo-3H,6H-1,4,5a,8a-tetraazaacenaphthylen-3-one

A mixture of 7.6 g of 4,5-dihydro-7-phenyl-pyrazolo[1,5-a]pyrimidine-3-carboxamide (prepared as described in Example 3) in 304 ml of dry tetrahydrofuran was stirred and cooled at −78° C. (dry-ice, acetone), under nitrogen and 2.17 g of sodium hydride (60% dispersion in mineral oil) was added. The mixture was stirred at −78° C. for 30 minutes, then 4.84 g of 1,1'-thiocarbonyldiimidazole was added in one portion. The temperature was kept at −78° C. for 2 hours, then was allowed to warm slowly to room temperature while stirring was continued for 48 hours. The reaction mixture was quenched with 500 ml of water and neutralized to pH 6–7 with 5% aqueous hydrochloric acid. A crystalline solid formed which was collected by filtration, triturated with ether, filtered and dried to give 3.2 g of the desired product as white crystals, m.p. 289°–291° C.

EXAMPLE 8

4,5-Dihydro-5-thioxo-8-[3-(trifluoromethyl)phenyl]3H,6H-1,4,5a,8a-tetraazaacenaphthylen-3-one To a stirred solution of 1.00 g of 4,5-dihydro-7-[3-(trifluoromethyl)phenyl]pyrazolo[1,5-a]pyrimidine-3-carboxamide (prepared as described in Example 4) in 30 ml of dry tetrahydrofuran cooled to −78° C. (dry ice-acetone) was added 286 mg of 60% sodium hydride (dispersion in mineral oil). The reaction mixture was stirred at −78° C. for 30 minutes then 637 mg of 1,1'-thiocarbonyldiimidazole was added. The mixture was allowed to slowly warm to room temperature and was stirred for 36 hours. The reaction mixture was quenched with water, neutralized with 5% aqueous hydrochloric acid and extracted with chloroform. Evaporation of the solvent in vacuo gave 934 mg of the desired product as a yellow solid, m.p. 251°–258° C. (dec).

EXAMPLE 9

5-(Methylthio)-8-[3-(trifluoromethyl)phenyl]-3H,6H-1,4,5a,8a-tetraazaacenaphthylen-3-one To a solution of 100 mg of 4,5-dihydro-5-thioxo-8-[3-(trifluoromethyl)phenyl]-3H,6H-1,4,5a,8a-tetraazaacenaphthylen-3-one (Example 8) in 10 ml of dry tetrahydrofuran, cooled at 0° C., was added 13 mg of sodium hydride (60% dispersion in mineral oil). The reaction mixture was stirred at 0° C. for 15 minutes, then an excess of methyl iodide was added. The mixture was allowed to warm to room temperature then was stirred for 3 hours. The mixture was quenched with water and extracted with chloroform. Evaporation of the extract in vacuo gave 47 mg of the product of the example as a yellow solid, m.p. 234°–237° C. (dec).

EXAMPLE 10

8-(3-Fluorophenyl)-4,5-dihydro-5-thioxo-3H,6H-1,4,5a,8a-tetraazaacenaphthylen-3-one A mixture of 63.0 g of 7-(3-fluorophenyl)-4,5-dihydropyrazolo[1,5-a]pyrimidine-3-carboxamide (Example 6) and 2.5 liters of dry tetrahydrofuran was stirred and cooled to −78° C. in a dry-ice-acetone bath, then 18.0 g of sodium hydride (60% dispersion in mineral oil) was added in one portion. This mixture was stirred at −78° C. for 1½ hours then 40.0 g of 1,1'-thiocarbonyl-diimidazole was added and stirring was continued at −78° C. for 2 hours. The mixture was allowed to warm to room temperature and was stirred for 48 hours, and then the reaction was quenched with 2.5 liters of water, neutralized with 5% aqueous hydrochloric acid. The crystalline solid that formed was collected, washed with ether and dried to give 54.6 g of the desired product as cream-colored crystals, m.p. 298°–300° C.

EXAMPLE 11

N-[3-Oxo-8-[3-(trifluoromethyl)phenyl]-3H,6H-1,4,5a,8a-tetraazaacenaphthylen-5-yl]benzamide To a stirred solution of 3.08 g of 4,5-dihydro-7-[3-(trifluoromethyl)phenyl]pyrazolo[1,5-a]pyrimidine-3-carboxamide (Example 4) in 30 ml of dry acetone, under nitrogen was added 1.5 ml of benzoyl isothiocyanate in 5 ml of dry acetone. The mixture was heated at reflux for 3 hours, then an additional 4.5 ml of benzoyl isothiocyanate was added and the mixture was heated at reflux for 16 hours. The mixture was cooled to room temperature and the solid precipitate that had formed was collected by filtration and washed with ether to give 600 mg of 4-[(benzoylamino)thioxomethyl]-4,5-dihydro-7-[3-(trifluoromethyl)phenyl]pyrazolo[1,5-a]pyrimidine-3-carboxamide, m.p. 210°–212° C. To a stirred mixture of 1.5 g of the preceding product (prepared as described above), 30 ml of N,N-dimethylformamide and 2.0 ml of 1N sodium hydroxide was added 4.0 ml of methyl iodide. This mixture was stirred at room temperature for 3 hours then an additional 1.0 ml of 1N sodium hydroxide and 2.0 ml of methyl iodide were added and stirring was continued. After one hour the addition of 1.0 ml of sodium hydroxide and 2.0 ml of methyl iodide was repeated and stirring was concluded within one hour of this addition. The mixture was mixed with water and the solid precipitate was collected by filtration, washed with water and dried in vacuo to give 1.4 g of 3-(aminocarbonyl)-N-benzoyl-7-[3-(trifluoromethyl)phenyl]pyrazolo[1,5-a]pyrimidine-4(5H)-carboximidothioic acid, methyl ester, m.p. 172°–175° C.

To a stirred mixture of 1.66 g of the preceding compound (prepared in the manner described above) in 30 ml of p-dioxane was added 30 ml of 7N sodium hydroxide. This mixture was heated at reflux for 2 hours. The two layer mixture was cooled, then neutralized to pH 7.0 with 6N hydrochloric acid. The solid which formed was collected by filtration, washed with water and dried. Recrystallization from acetonitrile gave 510 mg of N-[3-oxo-8-[3-(trifluoromethyl)phenyl]-3H,6H-1,4,5a,8a-tetraazaacenaphthylen-5-yl]benzamide as a white solid, m.p. 235°–239° C.

EXAMPLE 12

[[3-(Aminocarbonyl)-7-[3-(trifluoromethyl)phenyl]-pyrazolo[1,5-a]pyrimidin-4(5H)-yl]-thioxomethyl] carbamic acid, ethyl ester To a stirred solution of 3.0 g of 4,5-dihydro-7[3-(trifluoromethyl)phenyl]pyrazolo[1,5-a]pyrimidine-3-carboxamide (prepared as described in Example 4) in 90 ml of dry tetrahydrofuran, cooled to −78° C. was added 584 mg of sodium hydride (60% dispersion in mineral oil) in one portion. The reaction mixture was stirred at −78° C. for one hour followed by the addition of 2.55 g of ethoxycarbonyl isothiocyanate. The mixture was stirred at −78° C. for 2 hours then was allowed to warm slowly to room temperature. The reaction mixture was stirred at room temperature for 48 hours, then was quenched with water and extracted with ether. The aqueous layer was separated, neutralized with 5% hydrochloric acid and extracted with chloroform. The chloroform extracts were evaporated in vacuo to give the product of the example as a yellow solid.

EXAMPLE 13

[3-Oxo-8[3-(trifluoromethyl)phenyl]-3H,6H-1,4,5a,8a-tetraazaacenaphthylen-5-yl]carbamic acid, ethyl ester To a stirred solution of 300 mg of [[3-(amino carbonyl)-7-[3-(trifluoromethyl)phenyl]pyrazolo[1,5-a]pyrimidin-4(5H)-yl]-thioxomethyl]carbamic acid, ethyl ester (Example 12) in 15.0 ml of dry tetrahydrofuran cooled in an ice bath at 0° C. was added 30 mg of sodium hydride (60% dispersion in mineral oil) in one portion. After the evolution of gas ceased the mixture was stirred for an additional 30 minutes at 0° C., then 1.0 ml of methyl iodide was added and the reaction mixture was allowed to warm to room temperature with stirring for 2 hours. The mixture was quenched with water and diluted in water. The aqueous solution was extracted with chloroform. The chloroform extracts were combined and evaporated in vacuo and the residue was triturated with ether. The solid was collected by filtration to give the desired product as a white solid, m.p. 219°–220° C.

EXAMPLE 14

5-(2-Methylpropyl)-8-[3-(trifluoromethyl)phenyl]-3H,6H-1,4,5a,8a-tetraazaacenaphthylen-3-one To a solution of 500 mg of 4,5-dihydro-5-thioxo-8-[3-(trifluoromethyl)phenyl]-3H,6H-1,4,5a,8a-tetraazaacenaphthylen-3-one (prepared as described in Example 8) in 10.0 ml of N,N-dimethylformamide was added 1.5 ml of 1N sodium hydroxide. The reaction mixture was cooled to 0° C. in an ice bath, then 0.5 ml of 30% hydrogen peroxide was added to the mixture dropwise. The reaction mixture was stirred at 0° C. for 30 minutes, then 1.0 ml of isobutylamine was added in one portion and the mixture was allowed to warm to room temperature, then was stirred for 2 hours. The solid was collected by filtration and washed with water, then ether to give 223 mg of the product of the example as a white solid, m.p. 266°–268° C. Following the procedure of Example 14 and reacting, 4,5-dihydro-5-thioxo-8-[3-(trifluoromethyl)phenyl]3H,6H-1,4,5a,8a-tetraazaacenaphthylen-3-one with the appropriate primary aliphatic amine or cyclic secondary amine, the products of Examples 15–27 were obtained as set forth in Table III.

TABLE III

| Example | Amine | Product | MP °C. |
|---|---|---|---|
| 15 | Pyrrolidine | 5-(1-Pyrrolidinyl)-8-[3-(trifluoromethyl)phenyl]-3H,6H-1,4,5a,8a-tetraazaacenaphthylen-3-one | 255–256 (dec) |
| 16 | Isopropylamine | 5-[(1-Methylethyl)amino]-8-[3-(trifluoromethyl)phenyl]-3H,6H-1,4,5a,8a-tetraazaacenaphthylen-3-one | 257–260 (dec) |
| 17 | Aminoacetaldehyde dimethyl acetal | 5-[(2,2-Dimethoxyethyl)amino]-8-[3-(trifluoromethyl)phenyl]-3H,6H-1,4,5a,8a-tetraazaacenaphthylen-3-one | 220–221 (dec) |
| 18 | sec-Butylamine | 5-[(1-Methylpropyl)amino]-8-[3-(trifluoromethyl)phenyl]-3H,6H-1,4,5a,8a-tetraazaacenaphthylen-3-one | 245–247.5 (dec) |
| 19 | Piperidine | 5-(1-Piperidinyl)-8-[3-(trifluoromethyl)phenyl]-3H,6H-1,4,5a,8a,tetraazaacenaphthylen-3-one | 259–261 (dec) |
| 20 | N-(2-Aminoethyl) morpholine | 5-[[2-(4-Morpholinyl)ethyl]amino]-8-[3-(trifluoromethyl)phenyl]-3H,6H-1,4,5a,8a-tetraazaacenaphthylen-3-one | 241–243 (dec) |
| 21 | 2-Amino-1-phenylethanol | 5-[(2-Hydroxy-2-phenylethyl)amino]-8-[3-(trifluoromethyl)phenyl]-3H,6H-1,4,5a,8a-tetraazaacenaphthylen-3-one | 266–267 (dec) |
| 22 | n-Butylamine | 5-(Butylamino)-8-[3-(trifluoromethyl)phenyl]-3H,6H-1,4,5a,8a-tetraazaacenaphthylen-3-one | 257–259 (dec) |
| 23 | Ethanolamine | 5-[[(2-Hydroxyethyl)amino]8-[3-(trifluoromethyl)phenyl]-3H,6H-1,4,5a,8a-tetraazaacenaphthylen-3-one | 247.5–249 (dec) |
| 24 | Methylamine | 5-(Methylamino)-8-[3-(trifluoromethyl)phenyl]-3H,6H-1,4,5a,8a-tetraazaacenaphthylen-3-one | 288–290 (dec) |
| 25 | 2-Methylbenzylamine | 5-[[(2-Methylphenyl)methyl]amino]-8-[3-(trifluoromethyl)phenyl]-3H,6H-1,4,5a,8a-tetraazaacenaphthylen-3-one | 277–280 (dec) |
| 26 | Morpholine | 5-(4-Morpholinyl)-8-[3-(trifluoromethyl)phenyl]-3H,6H-1,4,5a,8a-tetraazaacenaphthylen-3-one | 240–243 (dec) |
| 27 | Diethylamine | 5-Ethylamino-8-[3-(trifluoromethyl)phenyl]-3H,6H-1,4,5a,8a-tetraazaacenaphthylen-3-one | 271–273 (dec) |

EXAMPLE 28

5-[(Phenylmethyl)amino]-8-[3-(trifluoromethyl)phenyl]-3H,6H-1,4,5a,8a-tetraazaacenaphthylen-3-one A 200 mg amount of 5-(methylthio)-8-[3-trifluoromethyl)phenyl]-3H,6H-1,4,5a,8a-tetraazaacenaphthylen- 3-one (prepared as described in Example 9) was suspended in 10.0 ml of benzylamine. The reaction mixture was cooled to room temperature and filtered. The solid on the filter was washed with ether and air dried to give 189 mg of the product of the example as a white solid, m.p. 220°–224° C.

EXAMPLE 29

5-Amino-8-[3-(trifluoromethyl)phenyl]-3H,6H-1,4,5a,8a-tetraazaacenaphthylen-3-one To a stirred solution of 556 mg of 4,5-dihydro-7-[3-(trifluoromethyl)phenyl]pyrazolo[1,5-a]pyrimidine-3-carboxamide (prepared as described in Example 4) in 25 ml of dry tetrahydrofuran, under nitrogen, cooled to −78° C. (dry-ice, acetone), was added 159 mg of sodium hydride (60% dispersion in mineral oil) in one portion. After stirring the mixture at −78° C. for 30 minutes, 191 mg of cyanogen bromide was added in one portion. The reaction mixture temperature was maintained at −78° C. for 4 hours, then was allowed to warm to room temperature over 16 hours. The mixture was diluted with water and the solid which separated was collected and washed with water and ether to give the product as a brown solid, m.p. 287°–289° C. (dec).

EXAMPLE 30

2,2,2-Trifluoro-N-[3-oxo-8-[3-(trifluoromethyl)phenyl]-3H,6H-1,4,5a,8a-tetraazaacenaphthylen-5-yl]acetamide A 750 mg amount of 5-amino-8-[3-(trifluoromethyl)phenyl]-3H,6H-1,4,5a,8a-tetraazaacenaphthylen-3-one (prepared as described in Example 29) was suspended in 20.0 ml of trifluoroacetic anhydride and this mixture was heated at reflux for 24 hours. The reaction mixture was filtered and the precipitate removed was washed with ether and chloroform. The filtrate was extracted with ether and chloroform and the combined organic solution was washed with saturated sodium bicarbonate, dried over magnesium sulfate and filtered. The filtrate was evaporated in vacuo to give 627 mg of the desired product as a white solid, m.p. 184°–185° C.

EXAMPLE 31

2-Chloro-N-[3-oxo-8-[3-(trifluoromethyl)phenyl]-3H,6H-1,4,5a,8a-tetraazaacenaphthylen-5-yl]acetamide A 500 mg amount of 5-amino-8-[3-(trifuoromethyl)phenyl]-3H,6H-1,4,5a,8a-tetraazaacenaphthylen-3-one (prepared as described in Example 29) was suspended and stirred in 30 ml of dry tetrahydrofuran, then 1 equivalent (0.322 g) of [1,8-bis(dimethylamino)-naphthalene,N,N,N′,N′-tetramethyl-1,8-naphthalenediamine] (Proton Sponge®) was added followed by 1.1 equivalents (0.187 g) of chloroacetyl chloride. The reaction mixture was heated at reflux for 16 hours, then allowed to cool to room temperature. The mixture was poured into 200 ml of water and the resulting precipitate was collected by filtration to give 423 mg of the product of the example as a brown solid, m.p. 189°–192° C. (dec).

EXAMPLE 32

[3-Oxo-8-[3-(trifluoromethyl)phenyl]-3H,6H-1,4,5a,8a-tetraazaacenaphthylen-5-yl)carbamic acid, 2,2,2-trichloroethyl ester A 500 mg amount of 5-amino-8-[3-(trifluoromethyl)phenyl]-3H,6H-1,4,5a,8a-tetraazaacenaphthylen-3-one (prepared as described in Example 29) was suspended and stirred in 25.0 ml of dry tetrahydrofuran, then 320 mg of [1,8-bis(dimethylamino)naphthalene,N,N, N′,N′-tetramethyl-1,8-naphthalenediamine] (Proton Sponge®) was added followed by 0.207 ml of 2,2,2-trichloroethyl chloroformate. This mixture was heated at reflux for 16 hours. The reaction mixture was quenched by pouring it into 200 ml of water and the precipitate formed was collected by filtration to give 419 mg of the desired product as a white solid, m.p. 225°–226° C.

EXAMPLE 33

4-Methoxy-N-[3-oxo-8-[3-(trifluoromethyl)phenyl]-3H,6H-1,4,5a,8a-tetraazaacenaphthylen-5-yl]benzamide A 200 mg amount of 5-amino-8-[3-(trifluoro-methyl)phenyl]-3H,6H-1,4,5a,8a-tetraazaacenaphthylen-3-one (prepared as described in Example 29) was suspended in 3 ml of pyridine, then 0.2 ml of p-methoxybenzoyl chloride was added in one portion and the reaction mixture was stirred at room temperature for 16 hours. The reaction was quenched in 100 ml of water and the solid which formed was collected by filtration and washed with ether to give 164 mg of the desired product as a white solid, m.p. 271°–273° C.

Following the procedure of Example 33 and reacting 5-amino-8-[3-(trifluoromethyl)phenyl]-3H,6H-1,4,5a,8a-tetraazaacenaphthylen-3-one with the appropriate acid chloride, the products of Examples 34–42 were obtained as set forth in Table IV.

TABLE IV

| Example | Acid Chloride | Product | MP °C. |
|---|---|---|---|
| 34 | 3-Trifluoromethylbenzoyl chloride | N-[3-Oxo-8-[3-(trifluoromethyl)phenyl]-3H,6H-1,4,5a,8a-tetraazaacenaphthylen-5-yl]-3-(trifluoromethyl)benzamide | 204–205 |
| 35 | p-Toluoyl chloride | 4-Methyl-N-[3-oxo-8-[3-(trifluoromethyl)phenyl]-3H,6H-1,4,5a,8a-tetraazaacenaphthylen-5-yl]benzamide | 278–280 |
| 36 | 2-Acetoxybenzoyl chloride | 2-(Acetyloxy)-N-[3-oxo-8-[3-(trifluoromethyl)phenyl]-3H,6H-1,4,5a,8a-tetraazaacenaphthylen-5-yl]benzamide | 232–236 |
| 37 | Phenoxyacetyl chloride | N-[3-Oxo-8-[3-(trifluoromethyl)phenyl]-3H,6H-1,4,5a,8a-tetraazaacenaphthylen-5-yl]-2-phenoxyacetamide | 180–182 |
| 38 | 3,5-Dimethoxybenzoyl chloride | 3,5-Methoxy-N-[3-oxo-8-[3-(trifluoromethyl)phenyl]-3H,6H-1,4,5a,8a-tetraazaacenaphthylen-5-yl]benzamide | 270–272 |
| 39 | 3-Nitrobenzoyl chloride | 3-Nitro-N-[3-oxo-8-[3-(trifluoromethyl)phenyl]-3H,6H-1,4,5a,8a-tetraazaacenaphthylen-5-yl]benzamide | 235–239 |
| 40 | 4-Bromobenzoyl chloride | 4-Bromo-N-[3-oxo-8-[3-(trifluoromethyl)phenyl]-3H,6H-1,4,5a,8a-tetraazaacenaphthylen-5-yl]benzamide | 269–274 (dec) |
| 41 | 3,4-Dichlorobenzoyl chloride | 3,4-Dichloro-N-[3-oxo-8-[3-(trifluoromethyl)phenyl]-3H,6H-1,4,5a,8a-tetraazaacenaphthylen-5-yl]benzamide | 256–260 |
| 42 | 4-Fluorophenylbenzoyl chloride | 4-Fluoro-N-[3-oxo-8-[3-(trifluoromethyl)phenyl]-3H,6H-1,4,5a,8a-tetraazaacenaphthylen-5-yl]benzamide | 267–269 |

EXAMPLE 43

5-[[(4-Chlorophenyl)methyl]amino]-8-[3-(trifluoromethyl)phenyl]-3H,6H-1,4,5a,8a-tetraazaacenaphthylen-3-one A 400 mg amount of 5-(methylthio)-8-[3-(trifluoromethyl)phenyl]-3H,6H-1,4,5a,8a-tetraazaacenaphthylen-3-one (prepared as described in Example 9) in 25.0 mg of 4-chlorobenzylamine was heated at 70° C. for 36 hours. The precipitate which formed was collected by filtration to give the product of the example as a white solid, m.p. 281°–282° C.

EXAMPLE 44

5-[(2-Methylpropyl)amino]-8-phenyl-3H,6H-1,4,5a,8a-tetraazaacenaphthylen-3-one

To a solution of 500 mg of 4,5-dihydro-8-phenyl-5-thioxo-3H,6H-1,4,5a,8a-tetraazaacenaphthylen-3-one (prepared as described in Example 7) in 10.0 ml of N,N-di-methylformamide was added 1.8 ml of 1N sodium hydroxide. The reaction mixture was cooled to 0° C. in an ice bath, then 0.6 ml of 30% hydrogen peroxide was added to the mixture dropwise. The reaction mixture was stirred at 0° C. for about 30 minutes, then 1.0 ml of isobutylamine was added in one portion and the mixture was allowed to warm to room temperature, then was stirred for 2 hours. The solid was collected and washed with water, then ether to give 253 mg of the desired product as a white solid, m.p. 265°–268° C. (dec). Following the procedure of Example 44 and reacting 4,5-dihydro-8-phenyl-5-thioxo-3H,6H-1,4,5a,8a-tetraazaacenaphthylen-3-one with the appropriate primary aliphatic amine or cyclic secondary amine, the products of Examples 45–51 were obtained as set forth in Table V.

TABLE V

| Example | Amine | Product | MP °C. |
|---|---|---|---|
| 45 | Aminoacetaldehyde dimethyl acetal | 5-[(2,2-Dimethoxyethyl)amino]-8-phenyl-3H,6H-1,4,5a,8a-tetraazaacenaphthylen-3-one | 223 |
| 46 | n-Butylamine | 5-(Butylamino)-8-phenyl-3H,6H-1,4,5a,8a-tetraazaacenaphthylen-3-one | 268–271 (dec) |
| 47 | Ammonia/methanol | 5-Amino-8-phenyl-3H,6H-1,4,5a,8a-tetraazaacenaphthylen-3-one | 291–294 (dec) |
| 48 | 70% Ethylamine/water | 5-(Ethylamino)-8-phenyl-3H,6H-1,4,5a,8a-tetraazaacenaphthylen-3-one | 290–291 (dec) |
| 49 | Isopropylamine | 5-[(Methylethyl)amino]-8-phenyl-3H,6H-1,4,5a,8a-tetraazaacenaphthylen-3-one | 278–279.5 |
| 50 | Ethanolamine | 5-[(2-Hydroxyethyl)amino]-8-phenyl-3H,6H-1,4,5a,8a-tetraazaacenaphthylen-3-one | 177–178 (dec) |
| 51 | 40% Methylamine/Water | 5-(Methylamino)-8-phenyl-3H,6H-1,4,5a,8a-tetraazaacenaphthylen-3-one | 265–268 (dec) |

EXAMPLE 52

8-(3-Fluorophenyl)-5-[(2-methylpropyl)amino]-3H,6H-1,4,5a,8a-tetraazaacenaphthylen-3-one To a solution or 3.00 g of 8-(3-fluorophenyl)-4,5-dihydro-5-thioxo-3H,6H-1,4,5a,8a-tetraazaacenaphthylen-3-one (Example 10) in 60.0 ml of N,N-dimethylformamide was added 10 ml of 1N sodium hydroxide. The reaction mixture was cooled to 0° C. in an ice bath, then 3.40 ml of 30% hydrogen peroxide was added to the mixture dropwise. The reaction mixture was stirred at 0° C. for 30 minutes, then 6.0 ml of isobutylamine was added in one portion and the mixture was allowed to warm to room temperature, then was stirred for 2 hours. The solid was collected by filtration, washed with water, then ether to give 1.24 g of the desired product as a white solid, m.p. 256°–259° C. Following the procedure of Example 52 and reacting 8-(3-fluorophenyl)-4,5-dihydro-5-thioxo-3H,6H-1,4,5a,8a-tetraazaacenaphthylen-3-one with the appropriate primary aliphatic amine or cyclic secondary amine, the products of Examples 53–57 were obtained as set forth in Table VI.

TABLE VI

| Example | Amine | Product | MP °C. |
|---|---|---|---|
| 53 | n-Butylamino | 5-(Butylamino)-8-(3-fluorophenyl)-3H,6H-1,4,5a,8a-tetraazaacenaphthylen-3-one | 255–257 |
| 54 | sec-Butyl- | 8-(3-Fluorophenyl)-5-[(1-amine methylpropyl)amino]-3H,6H-1,4,5a,8a-tetraazaacenaphthylen-3-one | 260–263 |
| 55 | 70% Aqueous Ethylamine | 5-(Ethylamino)-8-(3-fluorophenyl)-3H,6H-1,4,5a,8a-tetraazaacenaphthylen-3-one | 285–287 |
| 56 | Aminoacetaldehyde dimethyl acetal | 5-[(2,2-Dimethoxyethyl)amino]-8-(3-fluorophenyl)-3H,6H-1,4,5a,8a-tetraazaacenaphthylen-3-one | 204–208 |
| 57 | Isopropylamine | 8-(3-Fluorophenyl)-5-[(1-methylethyl)amino]-3H,6H-1,4,5a,8a-tetraazaacenaphthylen-3-one | 262–264 |

EXAMPLE 58

8-(3-Fluorophenyl)-5-[[3-(1H-imidazol-1-yl)propyl]amino]-3H,6H-1,4,5a,8a-tetraazaacenaphthylen-3-one To a stirred solution of 10.0 g of 8-(3-fluorophenyl)-4,5-dihydro-5-thioxo-3H,6H-1,4,5a,8a-tetraazaacenaphthylen-3one in 300 ml of N,N-dimethylformamide was added 18.75 ml of 1N sodium hydroxide. The reaction mixture was cooled to 0° C. in an ice bath for 30 minutes, then 6.25 ml of 30% hydrogen peroxide was added to the mixture dropwise. The mixture was stirred at 0° C. for one hour and 30 minutes then 12.5 ml of N(3-aminopropyl)imidazole was added in one portion. The mixture was allowed to warm to room temperature over 32 hours. The mixture was filtered to remove the solid which was washed with water. The filtrate and wash was evaporated in vacuo to give a yellow solid. The solid was dissolved in 250 ml of chloroform then 100 ml of water was added to give a precipitate. The layers were separated and the precipitate was collected by filtration to give a white solid. The solid was recrystallized from dimethylsulfoxide and dried in vacuo at 60° C. to give 1.1 g of the product of the example as a white solid, m.p. 256°–258° C.

EXAMPLE 59

5-[[3-(1H-Imidazol-1-yl)propyl]amino]-8-phenyl-3H,6H-1,4,5a,8a-tetraazaacenphthylen-3-one To a stirred solution of 5.0 g of 4,5-dihydro-8-phenyl-5-thioxo-3H,6H-1,4,5a,8a-tetraazaacenaphthylen-3-one (Example 7) in 200 ml of N-N-dimethylformamide was added 9.37 ml of 1N sodium hydroxide. The reaction mixture was cooled to 0° C. in an ice bath for 30 minutes then 3.125 ml of 30% hydrogen peroxide was added dropwise. After stirring the mixture at 0° C. for an additional 30 minutes 6.25 ml of N(3-aminopropyl) imidazole was added in one portion. Then the reaction mixture was allowed to warm to room temperature over a 24 hour period. The solvent was evaporated in vacuo to give a yellow oil. The oil was mixed with 250 ml of chloroform and the mixture was transferred to a separatory funnel. The organic layer was separated, dried over anhydrous sodium sulfate and filtered. The filtrate was evaporated in vacuo to give a yellow oil. This oil was triturated with ether to precipitate a white solid. The solid was collected by filtration, recrystallized from dimethylsulfoxide: ether, 2:1 and dried in vacuo at 70° C. to give 500 milligrams of the desired product as a white solid, m.p. 238°–240° C.

EXAMPLE 60

5-Amino-8-(3-fluorophenyl)-3H,6H-1,4,5a,8a-tetraazaacenaphthylen-3-one

To a stirred suspension of 5.0 g of 7-(3-fluorophenyl)-4,5-dihydropyrazolo[1,5-a]pyrimidine-3-carboxamide (Example 6) in 250 ml of dry tetrahydrofuran, cooled to −78° C. (dry-ice, acetone) was added 1.70 g of sodium hydride (60% dispersion in mineral oil) in one portion. The reaction mixture was stirred at −78° C. for 30 minutes then 2.05 g of cyanogen bromide was added and the mixture was stirred for an additional 2 hours at −78° C., then slowly allowed to warm to room temperature over 16 hours. The reaction mixture was diluted with water and the solid was collected by filtration, washed with water, then ether to give 376 mg of the desired product as a white solid.

EXAMPLE 61

N-[3-Oxo-8-[3-(trifluoromethyl)phenyl]-3H,6H-1,4,5a,-8a-tetraazaacenaphthylen-5-yl]-4-(phenylmethyl)-1-piperazineacetamide A 1.000 g amount of 2-chloro-N-[3-oxo-8-[3-(trifluoromethyl)phenyl]-3H,6H-1,4,5a,8a-tetraazaacenaphthylen-5-yl]acetamide (prepared in the manner described in Example 31) was dissolved in 50 ml of dry tetrahydrofuran, then 430 mg of 1-benzylpiperazine was added to the mixture in one portion. The reaction mixture was heated at reflux for 16 hours. The mixture was cooled, made basic with 1N sodium hydroxide and extracted with chloroform. The solvent was evaporated and the solid was purified by conventional means to give 426 mg of the desired product as a brown solid.

EXAMPLE 62

7-Methyl-5-[(1-methylethyl)amino]-8-[3-(trifluoromethyl)phenyl]-3H,6H-1,4,5a,8a-tetraazaacenaphthylen-3-one Following the procedure described in Example 2, 27.6 g of 6-methyl-7-(3-(trifluoromethyl)phenyl)-pyrazolo[1,5-a]pyrimidine-3-carbonitrile (disclosed in U.S. Pat. No. 4,178,449) gave 18.7 g of 6-methyl-7-[3-(trifluoromethyl)phenyl]pyrazolo[1,5-a]pyrimidine-3-carboxamide, m.p. 237°–239° C.

The preceding product (18.7 g was dissolved in 200 ml of glacial acetic acid by stirring for one hour, under nitrogen, in an ice bath then, 3.67 g of sodium cyanoborohydride was added to the reaction mixture, portionwise, under nitrogen. The solution was stirred for four hours and 30 minutes at room temperature, then was evaporated in vacuo to give an oil. The oil was triturated with saturated sodium bicarbonate solution to pH 7.0. The precipitate which formed was collected by filtration, washed with water and dried. The solid was dissolved in 200 ml of ethyl acetate, by heating on a steam bath, then hexane was added until crystals formed. After cooling the crystals were collected by filtration to give 22.0 g of 4,5-dihydro-6-methyl-7-[3-(trifluoromethyl)phenyl]pyra zolo[1,5-a]pyrimidine-3-carboxamide as white crystals, m.p. 200°–202° C.

To a stirred suspension of 5.0 g of the preceding dihydro compound in 200 ml of dry tetrahydrofuran, cooled to −78° C. (dry ice, acetone) was added 1.43 g of sodium hydride (60% dispersion in mineral oil) in one portion. The reaction mixture was stirred at −78° C. for 30 minutes, then 3.185 g of 1,1'-thiocarbonyldiimidazole was added in one portion. The stirred solution was kept at −78° C. for 2 hours, then the reaction mixture was allowed to slowly warm to room temperature over 24 hours. The mixture was quenched with 500 ml of water and neutralized with 5% aqueous hydrochloric acid. The crystals that formed on standing were collected and washed with ether to give 4.0 g of 4,5-dihydro-7-methyl-5-thioxo-8-[3-(trifluoromethyl)phenyl]-3H,6H-1,4,5a,8a-tetraazaacenaphthylen-3-one as white crystals, m.p. 269°–271° C.

To a stirred solution of 2.5 g of the above product in 150 ml of N,N,-dimethylformamide was added 7.5 ml of 1N sodium hydroxide. The reaction mixture was cooled to 0° C. in an ice bath for 30 minutes then 2.5 ml of 30% hydrogen peroxide was added dropwise and the mixture was stirred at 0° C. for one hour. The 5.0 ml of isopropylamine was added in one portion and the mixture was allowed to warm to room temperature over 72 hours. The precipitate that formed was collected by filtration, washed with water, then ether and dried to give 600 mg of the product of the example as white crystals, m.p. 284°–286° C.

EXAMPLE 63

8-(4-Chlorophenyl)-7-methyl-5-[(2-methylpropyl)amino]-3H,6H-1,4,5a,8a-tetraazaacenaphthylen-3-one A mixture of 50.0 g of p-chloropropiophenone and 200 ml of N,N-dimethylformamide dimethyl acetal was stirred and heated at reflux for 28 hours. The reaction mixture was evaporated in vacuo to give a yellow oil. The oil was then subjected to Kugelrohr distillation. The residual oil from the distillation was collected and triturated with hexane to provide crystals. The solid was collected by filtration and gave 21.5 g of 4'-chloro-3-dimethylamino-2-methylacrylophenone as yellow crystals, m.p. 45°–47° C.

A mixture of 21.5 g of the preceding compound, 10.368 g of 3-aminopyrazole-4-carbonitrile and 250 ml of glacial acetic acid was stirred and heated at reflux for 24 hours. The mixture was evaporated to dryness in vacuo to give brown crystals. The solid was triturated with saturated sodium bicarbonate solution to obtain pH 7–8 then the mixture was filtered. The solid was washed with water and dried to give 25.2 g of 7-(4-chlorophenyl)-6-methyl-pyrazolo[1,5-a]pyrimidine-3-carbonitrile as light brown crystals, m.p. 154°–157° C. A mixture of 18.8 g of the preceding compound and 100 ml of concentrated sulfuric acid was stirred at room temperature for 18 hours. The solution was then carefully poured into ice with stirring. The solid that formed was collected by filtration then neutralized with 1N sodium hydroxide, filtered and washed with water. The crystals were collected and dried to give 18.7 g of 7-(4-chloro-phenyl)-6-methylpyrazolo[1,5-a] pyrimidine-3-carboxamide.

A 17.7 g amount of the preceding product was dissolved in 200 ml of glacial acetic acid by stirring for one hour, under nitrogen, in an ice bath, then 3.88 g of sodium cyanoborohydride was added to the reaction mixture, portionwise, under nitrogen. The solution was stirred for two hours at room temperature, then was evaporated in vacuo to give an oil. The oil was triturated with saturated sodium bicarbonate solution to pH 7.0. The precipitate which formed was collected by filtration, washed with water and dried. The solid was recrystallized from absolute ethanol to give 12.6 g of 7-(4-chlorophenyl)-4,5-dihydro-6-methylpyrazolo[1,5-a]pyrimidine-3-carboxamide as white crystals, m.p. 210°–212° C.

To a stirred suspension of 5.0 g of the preceding dihydro compound in 200 ml of dry tetrahydrofuran, cooled to −78° C. (dry-ice, acetone) was added 1.43 g of sodium hydride (60% dispersion in mineral oil) in one portion. The reaction mixture was stirred at −78° C. for 30 minutes, then 3.185 g of 1,1'-thiocarbonyldiimidazole was added in one portion. The stirred solution was kept at −78° C. for 2 hours, then the reaction mixture was allowed to slowly warm to room temperature over 24 hours. The mixture was quenched with 500 ml of water and neutralized with 5% aqueous hydrochloric acid. The crystals that formed on standing were triturated with ether and filtered. The crystals were then added to a mixture of 1:1 methanol:chloroform, which was heated, cooled and filtered to give 4.2 g of 8-(4-chlorophenyl)-4,5-dihydro-7-methyl-5-thioxo-3H,6H-1,4-,5a,8a-tetraazaacenaphthylen-3-one as cream-colored crystals, m.p. 283°–285° C.

To a stirred solution of 4.0 g of the preceding compound in 100 ml of N,N-dimethylformamide was added 7.5 ml of 1N sodium hydroxide. The reaction mixture was cooled to 0° C. in an ice bath, then 2.5 ml of 30% hydrogen peroxide was added dropwise and the mixture was stirred at 0° C. for one hour. Then 5 ml of isobutylamine was added in one portion and the reaction mixture was allowed to warm to room temperature for 48 hours. The solution was evaporated in vacuo to give a light yellow solid. The solid was washed with water, then ether and dried to give 2.6 g of white solid. The solid was dissolved in 200 ml of isopropyl alcohol by warming then was cooled with scratching to precipitate the product. The product was collected by filtration to give 1.4 g of the product of the example as a white solid, m.p. 283°–285° C.

EXAMPLE 64

5-(Butylamino)-2,7-dimethyl-8-phenyl-3H,6H-1,4,5a,8a-tetraazaacenaphthylen-3-one A mixture of 57.0 g of propiophenone in 150 ml of N,N-dimethylformamide dimethyl acetal was stirred and heated at reflux for 24 hours. Then the solvent was removed in vacuo to give a yellow oil. The oil was subjected to Kugelrohr distillation to give 69.8 g of 3-dimethylamino-2-methylacrylophenone as a yellow oil, B.P. 100° C. (0.050 mm Hg).

A mixture of 37.6 g of the preceding compound and 24.3 g of 5-amino-3-methyl-4-pyrazolecarbonitrile in 500 ml of glacial acetic acid was stirred and heated at reflux for 48 hours. The solution was evaporated in vacuo to give a brown solid. The solid was neutralized to pH 7.0 with saturated sodium bicarbonate solution, filtered, washed with water and dried. The solid was heated on a steam bath in 800 ml of absolute ethanol and filtered to give 11.2 g of 2,6-dimethyl-7-phenyl-pyrazolo[1,5-a]pyrimidine-3-carbonitrile as a white solid, m.p. 208°–210° C.

A mixture of 22.8 g of the preceding product (prepared in the manner described above) and 300 ml of concentrated sulfuric acid was stirred at room temperature for 24 hours. The solution was then carefully poured into ice and gave a precipitate. The mixture was allowed to warm to room temperature and then was filtered to give a yellowish solid. The material was neutralized with 1N sodium hydroxide to pH 7.0, then washed with water and dried. The solid was heated in 900 ml of absolute ethanol then filtered to collect 8.2 g of 2,6-dimethyl-7-phenylpyrazolo[1,5-a] pyrimidine-3-carboxamide as a white solid, m.p. 252°–254° C. The filtrate was cooled and allowed to stand to crystallize an additional 14.7 g of product m.p. 252°–254° C.

A 22.9 g amount of the preceding product was dissolved in 300 ml of glacial acetic acid with stirring under nitrogen in an ice bath, then 13.51 g of sodium cyanoborohydride was added to the reaction mixture, portionwise. The reaction mixture was stirred at room temperature for 5 hours then the solution was evaporated in vacuo to give an oil. The oil was neutralized with saturated sodium bicarbonate solution to give a precipitate. The solid was collected by filtration, washed copiously with water and dried. The solid was dissolved by warming in 6000 ml of absolute ethanol. The solution was filtered and the filtrate was cooled in an ice bath and scratched to precipitate a solid. The solid was collected by filtration and dried in vacuo to give 13.6 g of 4,5-dihydro-2,6-dimethyl-7-phenyl-pyrazolo[1,5-a]pyrimidine-3-carboxamide as white crystals, m.p. 208°–210° C.

To a stirred suspension of 13.6 g of the preceding dihydro compound in 600 ml of dry tetrahydrofuran, cooled to −78° C. (dry-ice, acetone) was added 2.1 g of sodium hydride (60% dispersion in mineral oil) in one portion. The reaction mixture was stirred at −78° C. for 30 minutes, then 7.74 g of 1,1′-thiocarbonyldiimidazole was added in one portion. The stirred solution was kept at −78° C. for 2 hours, then the reaction mixture was allowed to slowly warm to room temperature over 24 hours. The reaction was quenched with 500 ml of water and neutralized with 5% aqueous hydrochloric acid. Crystals formed with stirring and were collected by filtration. The solid was triturated with ether, then collected to give 9.7 g of 4,5-dihydro-2,7-dimethyl-8-phenyl-5-thioxo-3H,6H-1,4,5a,8a-tetraazaacenaphthylen-3-one as white crystals, m.p. 255°–257° C.

To a stirred solution of 4.5 g of the preceding 3-one compound in 200 ml of N,N-dimethylformamide was added 8.43 ml of 1N sodium hydroxide in one portion. The reaction mixture was cooled to 0° C. in an ice bath, then 2.8 ml of 30% hydrogen peroxide was added dropwise and the mixture was stirred at 0° C. for one hour and thirty minutes. Then 5.62 ml of n-butylamine was added in one portion and the mixture was allowed to warm to room temperature over 48 hours. The solvent was evaporated in vacuo to give a white solid. The solid was then subjected to flash chromatography on silica gel using 2% methanol/98% chloroform as the solvent system. The desired fraction was collected and evaporated in vacuo to give 400 mg of the product of the example as a white solid, m.p. >300° C.

EXAMPLE 65

7-(3-methylphenyl)pyrazolo[1,5-a]pyrimidine-3-carboxamide

A mixture of 7-(3-methylphenyl)pyrazolo[1,5-a]pyrimidine-3-carbonitrile (prepared as described in Example 7 of U.S. Pat. No. 4,236,005) and concentrated sulfuric acid is stirred at room temperature for 16 hours. The solution is then carefully poured into ice with stirring and mixture is carefully made just basic with concentrated ammonium hydroxide. The solid is collected by filtration to give 7-(3-methylphenyl) pyrazolo[1,5-a]pyrimidine-3-carboxamide.

EXAMPLE 66

4,5-Dihydro-7-(3-methylphenyl)pyrazolo[1,5-a]pyrimidine-3-carboxamide

7-[3-Methylphenyl)pyrazolo[1,5-a]pyrimidine-3-carboxamine (prepared as described in Example 1) is stirred as a suspension in gacial acetic acid (cooled in an ice bath) under nitrogen and then excess sodium cyanoborohydide is added to the reaction mixture in portions. After one hour of stirring in the ice bath, the mixture is stirred at room temperature for 19 hours. This solution is evaporated to dryness, then water is added and the white precipitate which forms is collected by filtration and washed with an aqueous saturated solution of sodium bicarbonate, and finally with water. The solid is collected by filteration and dried to give 4,5-dihydro-7-(3-methylphenyl)pyrazolo[1,5-a]pyrimidine-3-carboxamide.

EXAMPLE 67

4,5-Dihydro-5-thioxo-8-)3-methylphenyl)-3H,6H-1,4,5a,8a-tetraazaacenaphthylen-3-one To a stirred solution of 1.00 g of 4,5-dihydro-7-(3-methyl)phenyl)pyrazolo[1,5-a]pyrimidine-3-carboxamide (prepared as described in Example 4) in dry tetrahydrofuran cooled to −78° C. (dry ice-acetone) is added sodium hydride (60% dispersion in mineral oil). The reaction mixture is stirred at −78° C. for 30 minutes then 1,1′-thiocarbonyldiimidazole is added. The mixture is allowed to slowly warm to room temperature and is stirred for 36 hours. Then reaction mixture is quenched with water, neutralized with 5% aqueous hydrochloric acid and extracted with chloroform. Evaporation of the solvent in vacuo gives 4,5-dihydro-5-thioxo-8-(3-methylphenyl)-3H,6H-1,4,5a,8a-tetraazaacenaphthylen-3-one.

EXAMPLE 68

8-(3-Methylphenyl)-5-[(2-methylpropyl)amino]-3H,6H-1,4,5a,8a-tetraazaacenaphthylen-3-one To a solution of 8-(3-Methylphenyl)-4,5-dihydro-5-thioxo-3H,6H-1,4,5a,8a-tetraazaacenaphthylen-3-one (Example 10) in N,N-dimethylformamide is added 1N sodium hydroxide. The reaction mixture is cooled to 0° C. in an ice bath, then 30% hydrogen peroxide is added dropwise and the reaction mixture is stirred at 0° C. for 30 minutes.

Isobutylamine is then added in one portion of the mixture is allowed to warm to room temperature, and it is stirred for 2 hours. The solid product is collected by filtration, washed with water and water and then ether to give 8-(3-methylphenyl)-5-[(2-methylpropyl)amino]-3H,6H-1,4,5a,8a-tetraazaacenaphthylen-3-one.

EXAMPLE 69

7-(3-Methoxyphenyl)Pyrazolo[1,5-a]pyrimidine-3-carboxamide

A mixture of 7-(3-methoxyphenyl)pyrazolo [1,5-a]pyrimidine-3-carbonitrile (prepared as describes in U.S. Pat. No. 4,236,005) and concentrated surfuric acid is stirred at room temperature for 4 hours and the resultant solution is then poured into an ice-water mixture with stirring. The precipitate is collected and dried to give 7-(3-methoxyoxyphenyl) pyrazolo[1,5-a] pyrimidine-3-carboxamine.

EXAMPLE 70

4,5-Dihydro-7-(3-methoxyphenyl)pyrazolo[1,5-a]pyrimidine 7-(3-Methyoxyphenyl)pyrazolo(1,5-a]pyramidine-3-carboxamide (prepared as described in Example 2) is stirred under nitrogen as a suspension in glacial acetic acid (cooled in an ice bath) and then excess sodium cyanoborohydide is added to the reaction mixture in portions. After one hour of stirring in the ice bath, the mixture is stirred at room temperature for 3 hours and then this solution is concentrated in vacuo. Water is added to the residue and the precipitate which forms is collected by filtration and then is dissolved in dichloromethane. The organic solution is washed with the saturated solution of sodium bicarbonate, dried over anhydrous sodium sulfate and filtered. The filtrate is evaporated in vacuo to give 4,5-dihydro-7-(3-methoxyphenyl)pyrazolo[1,5a] pyramidine as a solid.

EXAMPLE 71

4,5-Dihydro-8-(3-methoxyphenyl)-5-thioxo-3H,6H-1,4,5a,8a-tetraazaacenaphthylen-3-one A mixture of 4,5-dihydro-7-(3-methyoxyphenyl)-pyrazolo1,5-a]pyrimidine-3-carboxamide (prepared as described in Example 3) in dry tetrahydrofuran is stirred and cooled at −78° C. (dry-ice, acetone), under nitrogen and two equivalents of sodium hydride (60% dispersion in mineral oil) is added. The mixture is stirred at 78° C. for 30 minutes, then 1,1'-thiocarbonyl-diimidazole is added in one portion. The temperature is kept at −78° C. for 2 hours, then the mixture is allowed to warm slowly to room temperature while stirring is continued for 48 hours. The reaction mixture is quenched with water and neutralized to pH 6–7 with 5% aqueous hydrochloric acid. A crystalline solid forms which is collected by filtration, triturated with ether, filtered and dried to give 4,5-dihydro-8-(3-methoxyphenyl)-5-thioxo-3H,6H-1,4,5a,8a-tetraazaacenaphthylen-3-one.

EXAMPLE 72

8-(3-Methoxyphenyl)-5-[2-methylpropyl)amino]-3H,6H-1,4,5a,8a-tetraazaacenaphthylen-3-one By the method of Example 68 8-(3-methoxyphenyl)4,5-dihydro-5,thioxo-3H,6H-1,4,5a,8a-tetraazaacenaphthylene-3-one is reacted with isobutylamine to give 8-(3-methoxyphenyl)-5-[(2-methylpropyl)amino]-3H,6H-1,4,5a,8a-tetraazaacenaphthylene-3-one.

We claim:
1. A compound of the formula:

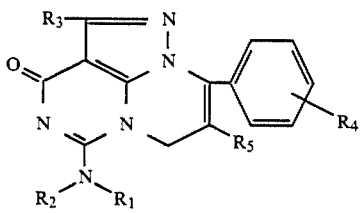

wherein $R_1$ and $R_2$ are each individually selected from the group consisting of hydrogen, alkyl($C_1$-$C_4$), benzoyl, mono or disubstituted benzoyl wherein the substituents are alkyl($C_1$-$C_6$), alkoxy($C_1$-$C_6$), acyloxy($C_2$-$C_7$), halogen, nitro or trifluoromethyl, and moieties of the formulae:

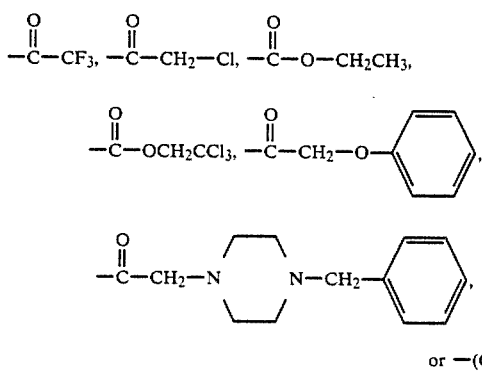

or —$(CH_2)_n$—R wherein n is an integer from 1 to 3 and R is hydroxy, 4-morpholinyl, 1H-imidazol-1-yl, —CH[alkoxy(C-$_1$-$C_3$)]$_2$, α-hydroxybenzyl, phenyl or mono or disubstituted phenyl wherein the substituents are halogen or alkyl($C_1$-$C_6$); $R_1$ and $R_2$ taken together with their associated (Nitrogen) is 4-morpholinyl or a moiety of the formula: —N$(CH_2)_m$ wherein m is an integer from 2 to 6; $R_3$ is hydrogen or alkyl($C_1$-$C_6$); $R_4$ is hydrogen, halogen, alkoxy($C_1$-$C_3$), alkyl($C_1$-$C_3$) or trifluoromethyl; and $R_5$ is hydrogen or alkyl($C_1$-$C_6$).

2. The compound in accordance with claim 1, 5-(2-methylpropyl)-8-[3-(trifluoromethyl)phenyl]-3H,6H-1,4-5a,8a-tetraazaacenaphthylen-3-one.

3. The compound in accordance with claim 1, 5-amino-8[3-(trifluoromethyl)phenyl]-3H,6H-1,4,5a,8a-tetraazaacenaphthylen-3-one.

4. The compound in accordance with claim 1, N-[3-oxo-8-[3-(trifluoromethyl)phenyl]-3H,6H-1,4,5a-8a-tetraazaacenaphthylen-5-yl]-3-(trifluoromethyl) benzamide.

5. The compound in accordance with claim 1, 3,4-dichloro-N-[3-oxo-8-[3-trifluoromethyl)phenyl]-3H,6H-1,4,5a,8a-tetraazaacenaphthylen-5-yl] benzamide.

6. The compound in accordance with claim 1, 5-ethylamino-8-[3-(trifluromethyl)phenyl]-3H,6H-1,4,5a,-8a-tetraazaacenaphthylen-3-one.

7. The compound in accordance with claim 1, [3-oxo-8-[3-(trifluoromethyl)phenyl]-3H,6H-1,4,5a,8a-tetraazaacenaphthylen-5-yl]carbamic acid, 2,2-trichloroethyl ester.

8. The compound in accordance with claim 1, 5-[2,2-dimethoxyethyl)amino]-8-[3-(trifluoromethyl)-phenyl]-3H,6H-1,4,5a,8a-tetraazaacenaphthylen-3-one.

9. The compound in accordance with claim 1, 5-(butylamino)-8-phenyl-3H,6H-1,4,5a,8a-tetraazaacenaphthylen-3-one.

10. The compound in accordance with claim 1, 5(ethylamino)-8-phenyl-3H,6H-1,4,5a,8a-tetraazaacenaphthylen-3-one.

11. The compound in accordance with claim 1, 5-(methylamino)-8-phenyl-3H,6H-1,4,5a,8a-tetraazaacenaphthylen-3-one.

12. The compound in accordance with claim 1, 5-[[(2-hydroxyethyl)amino]-8-[3-(trifluoromethyl)phenyl]-3H,6H-1,4,5a,8a-tetraazaacenaphthylen-3-one.

13. The compound in accordance with claim 1, 5-(ethylamino)-8-(3-fluorophenyl)-3H,6H-1,4,5a,8a-tetraazaacenaphthylen-3-one.

14. The compound in accordance in claim 1, 8-(4-chlorophenyl)-7-methyl-5-[(2-methylpropyl)amino]-3H,6H-1,4,5a,8a-tetraazaacenaphthylen-3-one.

15. The compound in accordance with claim 1, 8-(3-fluorophenyl)-5-[[3-(1H-imidazol-1-yl)propyl]amino-3H,6H-1,4,5a,8a-tetraazaacenaphthylen-3-one.

16. The compound in accordance with claim 1, 3-nitro-N-[3-oxo-8-[3-(trifluoromethyl)phenyl]-3H,6H-1,4,5a,8a-tetraazaacenaphthylen-5-yl]benzamide.

17. A method for the treatment of cognitive and related neural behavioral disorders in warm-blooded animals affected with such a disorder which comprises administering to said warm-blooded animal a therapeutically effective amount of a compound of claim 1.

18. A therapeutic composition of matter in dosage unit form for the treatment of cognitive and related neural behavioral disorders in warm-blooded animals comprising from about 50 mg to about 250 mg per dosage unit of a compound of claim 1 in association with a pharmaceutically acceptable carrier.

* * * * *